(12) United States Patent
Wang et al.

(10) Patent No.: US 9,173,424 B2
(45) Date of Patent: Nov. 3, 2015

(54) PYRIDINE DERIVATIVES WITH UMAMI FLAVOUR

(75) Inventors: Yili Wang, Mason, OH (US); Andrew Daniher, Cincinnati, OH (US); Adri De Klerk, Made (NL); Cornelis Winkel, Bussum (NL)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 13/381,393

(22) PCT Filed: Jul. 10, 2010

(86) PCT No.: PCT/EP2010/059916
§ 371 (c)(1),
(2), (4) Date: Jan. 19, 2012

(87) PCT Pub. No.: WO2011/004016
PCT Pub. Date: Jan. 13, 2011

(65) Prior Publication Data
US 2012/0121783 A1 May 17, 2012

Related U.S. Application Data

(60) Provisional application No. 61/224,604, filed on Jul. 10, 2009, provisional application No. 61/235,452, filed on Aug. 20, 2009.

(51) Int. Cl.
| | | |
|---|---|---|
| A23L 1/226 | (2006.01) | |
| C07D 405/00 | (2006.01) | |
| C07D 213/46 | (2006.01) | |
| A23L 1/22 | (2006.01) | |
| C07D 213/50 | (2006.01) | |
| C07D 405/06 | (2006.01) | |
| C07D 405/10 | (2006.01) | |

(52) U.S. Cl.
CPC ......... *A23L 1/22678* (2013.01); *A23L 1/22008* (2013.01); *A23L 1/2265* (2013.01); *A23L 1/22628* (2013.01); *A23L 1/22671* (2013.01); *C07D 213/46* (2013.01); *C07D 213/50* (2013.01); *C07D 405/00* (2013.01); *C07D 405/06* (2013.01); *C07D 405/10* (2013.01)

(58) Field of Classification Search
CPC .............. A23L 1/22008; A23L 1/2265; A23L 1/22671; A23L 1/22628; A23L 1/22678; A23L 1/226; C07D 405/00; C07D 405/10; C07D 405/06; C07D 213/46; C07D 213/50
USPC .............. 426/534, 536, 537, 538, 650; 546/1, 546/192, 193, 283.7, 340
See application file for complete search history.

(56) References Cited

U.S. PATENT DOCUMENTS

| | | | |
|---|---|---|---|
| 3,956,375 A | 5/1976 | Farkas et al. | |
| 3,976,790 A | 8/1976 | Crosby et al. | |
| 5,731,292 A * | 3/1998 | Tsujihara et al. | 514/25 |
| 8,715,761 B2 * | 5/2014 | Daniher et al. | 426/548 |
| 2010/0040753 A1 | 2/2010 | Daniher et al. | |
| 2010/0233102 A1 | 9/2010 | Krammer et al. | |
| 2011/0020518 A1 | 1/2011 | Delort et al. | |

FOREIGN PATENT DOCUMENTS

| | | |
|---|---|---|
| FR | 2 164 676 A1 | 8/1973 |
| WO | WO 2007/107596 A1 | 9/2007 |
| WO | WO 2009/105906 A1 | 9/2009 |
| WO | WO 2009/122318 A1 | 10/2009 |

OTHER PUBLICATIONS

GB 0913804.1—Great Britain Search Report, Nov. 20, 2009.
PCT/EP2010/059916—Written Opinion of the International Searching Authority, Oct. 4, 2010.
PCT/EP2010/059916—International Search Report, Oct. 4, 2010.

\* cited by examiner

*Primary Examiner* — Leslie Wong
(74) *Attorney, Agent, or Firm* — Curatolo Sidoti Co., LPA; Joseph G. Curatolo; Salvatore A. Sidoti

(57) ABSTRACT

A compound (including salts thereof) according to Formula I

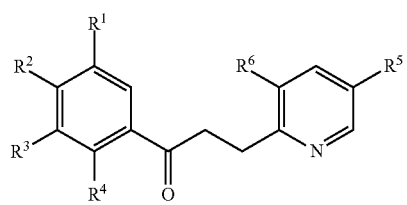

in which
$R^1$ is H, methyl or ethyl;
$R^2$ is H, OH, fluorine, $C_1$-$C_4$ linear or branched alkyl, $C_1$-$C_6$ alkoxy wherein the alkyl group is linear or branched, or a $C_3$-$C_5$ cycloalkyl moiety;
$R^3$ is H, methoxy, methyl or ethyl;
or $R^2$ and $R^3$ together form a bridging moiety —O—$CH_2$—O— between the phenyl carbon atoms to which they are connected;
$R^4$ is OH or methoxy; and
$R^5$ and $R^6$ are independently H or methyl;
$R^1$, $R^2$, $R^3$, $R^4$, $R^5$ and $R^6$ are such that,
(i) when $R^2$ and $R^3$ together form a bridging moiety —O—$CH_2$—O— between the phenyl carbon atoms to which they are connected, $R^1$, $R^5$, $R^6$ are H, and $R^4$ is OH; and
(ii) when $R^4$ is OH and $R^1$-$R^3$ are H, at least one of $R^5$, $R^6$ is methyl.

6 Claims, No Drawings

PYRIDINE DERIVATIVES WITH UMAMI FLAVOUR

CROSS REFERENCE TO RELATED APPLICATIONS

This application is a national stage application of International Application No. PCT/EP2010/059916, filed 9 Jul. 2010, which claims priority from U.S. Provisional Patent Application Ser. No. 61/224,604, filed 10 Jul. 2009, and from U.S. Provisional Patent Application Ser. No. 61/235,452, filed 20 Aug. 2009, from which applications priority is claimed, and which are incorporated herein by reference.

This disclosure relates to chemical compounds and to their use in flavouring.

Umami is a flavour sensation generally associated with Asian cuisine. In addition, improved umami taste helps make low salt products more palatable. Umami flavour has traditionally been achieved by the addition of monosodium glutamate (MSG) to foodstuffs. However, the presence of MSG in foodstuffs is not universally welcome. and there is an interest in the achievement of umami taste without MSG.

It has been found that certain compounds confer desirable umami taste sensations on compositions intended to be taken orally. There is therefore provided a compound (including salts thereof) according to Formula I

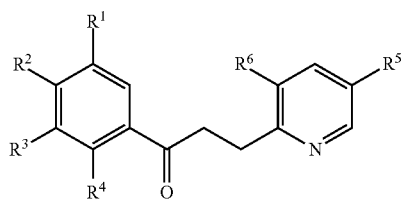

in which
R$^1$ is selected from methyl and ethyl;
R$^2$ is selected from H, OH, fluorine, C$_1$-C$_4$ linear or branched alkyl, C$_1$-C$_6$ alkoxy wherein the alkyl group is linear or branched, or comprises or consists of a C$_3$-C$_5$ cycloalkyl moiety;
R$^3$ is selected from H, methoxy, methyl and ethyl;
or R$^2$ and R$^3$ together form a bridging moiety —O—CH$_2$—O— between the phenyl carbon atoms to which they are connected;
R$^4$ is selected from OH and methoxy; and
R$^5$ and R$^6$ are independently selected from H and methyl;
R$^1$, R$^2$, R$^3$, R$^4$, R$^5$ and R$^6$ being selected such that,
(i) when R$^2$ and R$^3$ together form a bridging moiety —O—CH$_2$—O— between the phenyl carbon atoms to which they are connected, R$^1$, R$^5$, R$^6$ are H, and R$^4$ is OH; and
(ii) when R$^4$ is OH and R$^1$-R$^3$ are H, at least one of R$^5$, R$^6$ is methyl.

In a particular embodiment, R$^3$ is selected from H and methoxy.

In a particular embodiment, R$^2$ is selected from H, OH, fluorine, methyl, C$_1$-C$_6$ alkoxy wherein the alkyl group is linear or branched, or comprises or consists of a C$_3$-C$_5$ cycloalkyl moiety.

In a further particular embodiment, R$^2$ is selected from methyl, methoxy and isobutyloxy, R$^3$ is H, R$^4$ is OH and R$^5$ and R$^6$ are H.

In a further particular embodiment, the compound (including salts thereof) of Formula I is selected from the group consisting of:

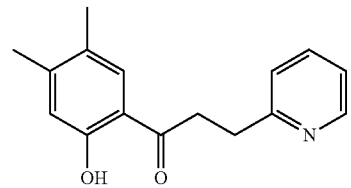

1-(2-hydroxy-4,5-dimethylphenyl)-3-(pyridine-2-yl)propan-1-one;

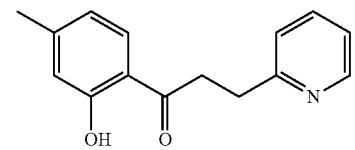

1-(2-hydroxy-4-methylphenyl)-3-(pyridin-2-yl)propan-1-one;

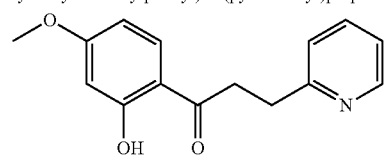

1-(2-hydroxy-4-methoxyphenyl)-3-(pyridin-2-yl)propan-1-one; and

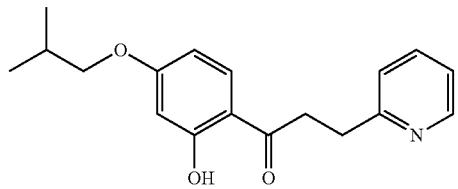

1-(2-hydroxy-4-isobutoxyphenyl)-3-(pyridine-2-yl)propan-1-one.

Other particular embodiments include (but are not limited to):

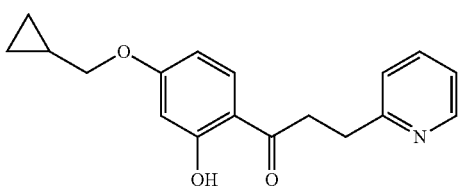

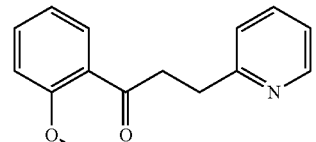

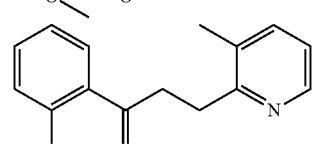

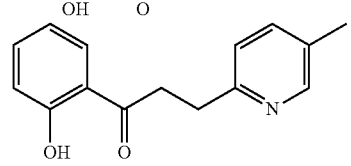

-continued

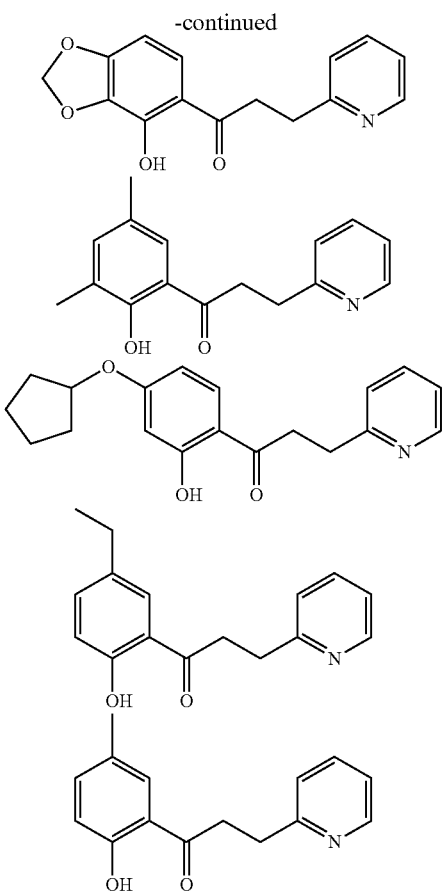

The compounds may be made by methods well known to the art. Non-limiting examples of suitable methods include:

1. Claisen-Schmidt condensation of an aromatic aldehyde with a substituted acetophenone. The base used for this condensation is sodium methoxide in methanol.

The reactions were performed in an organic solvent (in particular, THF). The obtained intermediate was hydrogenated in methanol with hydrogen and 10% palladium on carbon as a catalyst.

2. Friedel-Craft acylation of the substituted phenol with 2-pyridinyl-propionic acid derivatives.

3. A one-step reaction of 2-hydroxyacetophenone with pyridin-2-ylmethanol and $RuCl_2(Me_2SO)_4$ as a catalyst in dioxane solvent.

4. A one-step reaction of 2-hydroxyacetophenone with isonicotinaldehyde was used with $RuCl_2(PPh_3)_3$ as a catalyst in dioxane solvent.

Not all of these methods will work for all compounds, but the selection of a particular method for a given compound is well known within the skill of the art.

The compounds hereinabove described may be used individually or in combinations, either with other such compounds, or other umami flavourants, or both. Other umami flavorants include, but are not limited to MSG, GMP (guanosine monophosphate) and IMP (inosine mono phosphate). There is therefore also provided a method of adding umami flavour to a consumable composition, comprising the addition to the composition of at least one compound of the Formula I.

By "consumable composition" is meant any composition that is taken into the mouth for ultimate spitting out or ingestion. The composition may be in any physical form, solid, liquid or gaseous. Non-limiting examples include all food products, food additives, nutraceuticals, pharmaceuticals and any product placed in the mouth including (but not limited to) chewing gum, oral care products, and oral hygiene products including but not limited to, cereal products, rice products, tapioca products, sago products, baker's products, biscuit products, pastry products, bread products, confectionery products, dessert products, gums, chewing gums, flavor or flavor-coated food/beverage containers, yeast products, baking-powder, salt and spice products, snack foods, savoury products, mustard products, vinegar products, sauces (condiments), soups, seasonings, ready-to-eat meals, gravies, nuts & nut products, tobacco products, cigars, cigarettes, processed foods, vegetable products, meat and meat products, egg products, milk and dairy products, yoghourts, cheese products, butter and butter substitute products, milk substitute products, soy products, edible oils and fat products, medicaments, beverages, carbonated beverages, alcoholic drinks such as beers, wines and spirits, non-alcoholic drinks such as soft drinks, including forms requiring reconstitution including, without limitation, beverage powder, milk based beverage powder, sugar-free beverage powder, beverage syrup, beverage concentrate, coffee and tea, food extracts, plant extracts, meat extracts, condiments, gelatins, pharmaceutical and non-pharmaceutical gums, tablets, lozenges, drops, emulsions, elixirs, syrups and other preparations for making beverages, and combinations thereof.

There is therefore provided an umami-flavored consumable composition comprising a product base and at least one compound as hereinabove described. By "product base" is meant the combination of all the usual art-recognised ingredients required for the particular consumable composition.

The concentrations at which the compounds hereinabove described may be used will naturally vary, depending on the taste desired, the nature of the other ingredients and the desired end-use. Typically the concentration will vary between 0.01-100 ppm, but it is to be emphasised that this is only an indication of a typical useful concentration, and that there will be circumstances in which it may be possible to formulate outside this range. More particular ranges are 0.1-50 ppm and 0.2-10 ppm.

The form in which the compounds hereinabove described may be used may vary. In addition to powders, liquids, solutions, dispersions or emulsions, they may be used in spray-dried or encapsulated forms.

The umami-flavoured consumable compositions may also contain any of the standard ingredients used in making such compositions, in art-recognised quantities. Non-limiting examples include food additives such as sweeteners, emulsifiers, yeast extracts, hydrolyzed vegetable proteins, short chain peptides, amino acids, fermented products, enzyme digests, Maillard reaction products and botanical extracts.

In addition to at least one of the subject compounds, the umami flavor may contain flavoring materials well known to those skilled in the art, including the materials on the FEMA GRAS list and the EU positive list. Flavor materials commonly provide aroma which in itself, can help improve the overall umami profile of the product. However, some flavor materials also have taste effects which, when used with the compounds hereinabove described, improve or enhance the umami taste sensation or improve the overall profile.

In addition, other materials on the approved list of flavor materials provide a umami taste or umami-like character or may enhance the overall umami taste. Some examples from the FEMA GRAS which may be used with the subject compounds include items, such as, N1-(2-methoxy-4-methylbenzyl)-N2-(2-(pyridin-2-yl)ethyl)oxalamide (FEMA#4231), N-(heptan-4-yl)benz0[D][1,3]dioxole-5-carboxamide (FEMA#4232), N1-(2,4-dimethoxybenzyl)-N2-(2-(pyridin-2-yl)ethyl)oxalamide (FEMA#4233), N1-(2-methoxy-4-methylbenzyl)-N2-(2-(5-methylpyridin-2-yl)ethyl)oxalamide (FEMA#4234), N-gluconyl ethanolamine(FEMA #4254), N-gluconyl ethanolamine phosphate (FEMA #4255), N-lactoyl ethanolamine (FEMA #4256), N-lactoyl ethanolamine phosphate (FEMA #4257), N-3,7-dimethyl-2,6-octadienyl-cyclopropylcarboxamide (FEMA #4267) and gamma aminobutyric acid.

There now follows a series of non-limiting examples, which describe particular embodiments.

EXAMPLE 1

Synthesis of 1-(2-hydroxy-4,5-dimethylphenyl)-3-(pyridine-2-yl)propan-1-one

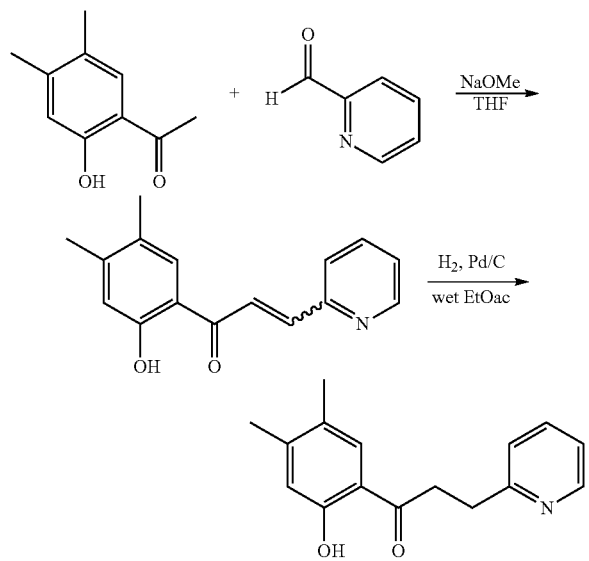

To a stirring solution of picolinaldehyde (1.52 g, 14.1 mmol) in THF (50 ml) and 7 ml 25% wt NaOMe was added 1-(2-hydroxy-4,5-dimethylphenyl)ethanone in 5 ml THF dropwise at room temperature (2.33 g, 14.1 mmol). The solution was continuously stirred at room temperature for 5 hours, and then water was added to the reaction flask. The aqueous layer was acidified to pH=7 using 1N HCl and extracted three times with EtOAc. The organic layers combined and dried ($Na_2SO_4$). The solvent was removed in vacuo and the residue chromatographed on silica gel (15% EtOAc/Hex) to yield 1.17 g of yellow product (32%).

$^1$H NMR (300 MHz, $CDCl_3$): δ 12.64 (s, 1H), 8.75 (d, J=5.1 Hz, 1H), 8.29 (d, J=15.9 Hz, 1H), 7.88-7.78 (m, 3H), 7.52 (d, J=8.4 Hz, 1H), 7.35 (d, d, d, J=1.5, 6.0, 9.0 Hz, 1H), 6.85 (s, 3H), 2.31 (s, 3H), 2.28 (s, 3H).

In a 250 ml round-bottom flask, (E)-1-(2-hydroxy-4,5-dimethylphenyl)-3-(pyridine-2-yl)prop-2-en-1-one (1.17 g, 4.62 mmol) and 0.18 g of 10% Pd/C were mixed together in wet EtOAc. Hydrogenation was conducted at atmospheric pressure, then the catalyst was filtered off. The crude product was purified by chromatography on silica gel (20% EtOAc/hexane) to provide 0.58 g (47.7%) of final compound.

$^1$H NMR (300 MHz, $CDCl_3$): δ 2.12 (s, 1H), 8.55 (d, J=5.1 Hz, 1H), 7.62 (d, d, d, J=2.1, 7.5, 9.6 Hz, 1H), 7.56 (s, 1H), 7.27 (d, J=7.5 Hz, 1H), 7.14 (d, d, J=4.5, 5.7 Hz, 1H), 6.77 (s, 1H), 3.52 (t, J=7.8 Hz, 2H), 3.25 (t, J=7.5 Hz, 2H), 2.26 (s, 3H), 2.21 (s, 3H).

EXAMPLE 2

Synthesis of 1-(2,4-dihydroxyphenyl)-3-(pyridine-2-yl)propan-1-one

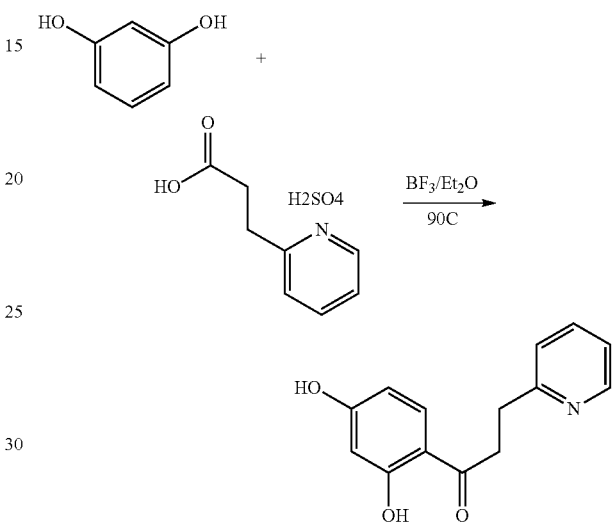

A mixture of resorcinol (2.2 g, 20 mmol), 3-pyridin-2-yl-propionic acid sulphuric acid salt (5 g, 20 mmol) and 50 ml boron trifluoride diethyl etherate ($BF_3.Et_2O$) was stirred at 90 C for 5 hours under $N_2$ (monitored by TLC). The reaction mixture was poured into 10% aqueous NaOAc solution and allowed to stand for 30 min and the solution was neutralized to pH=7 by 1M HCl and was extracted with EtOAc (3×50 ml). The combined EtOAc layer was washed with water, brine and dried over $Na_2SO_4$. The residue obtained after evaporation of the solvent was chromatographed over silica gel column using hexane-EtOAc mixture (1:1) as eluent to give mixture of products, which was then recrystallized in hot MTBE/Hex to afford final product (24%) with >97% purity.

$^1$H NMR (300 mHz, $CD_3OD$) δ 8.46-8.44 (d,d,d, J=5.1, 1.8, 0.9 Hz, 1H), 7.78-7.72 (d, d, d, J=9.9, 7.8, 2.1 Hz, 1H), 7.78-7.75 (d, J=8.7 Hz, 1H), 7.40-7.37 (d, J=8.1 Hz, 1H), 7.29-7.23 (d,d, d, J=6.3, 4.8, 1.2 Hz, 1H), 6.38-6.34 (d, d, J=9.0, 2.4 Hz, 1H), 6.26-6.25 (d, J=2.4 Hz, 1H), 3.41 (t, J=7.5 Hz, 2H), 3.18 (t, J=8.4 Hz, 2H).

EXAMPLE 3

1-(2-hydroxy-4-methylphenyl)-3-(pyridin-2-yl)propan-1-one

The title compound was synthesized using the same procedure as described in example 1.

$^1$H NMR (300 MHz, $CDCl_3$): δ 12.29 (s, 1H), 8.53 (d, J=4.5 Hz, 1H), 7.63 (d, d, d, J=3.0, 9.6, 11.7 Hz, 1H), 7.26 (d, J=7.2 Hz, 1H), 7.14 (d, d, d, J=1.2, 5.4, 7.8 Hz, 1H), 6.79 (s, 1H), 6.71 (d, d, J=1.8, 8.4 Hz, 1H), 3.53 (t, J=7.2 Hz, 2H), 3.24 (t, J=7.2 HZ, 2H), 2.36 (s, 3H).

EXAMPLE 4

1-(2-hydroxy-4-methoxyphenyl)-3-(pyridin-2-yl)propan-1-one

The title compound was synthesized using the same procedure as described in example 1.

$^1$H NMR (300 MHz, CDCl$_3$): δ 12.77 (s, 1H), 8.53 (d, J=4.8 Hz, 1H), 7.72 (d, d, J=2.7, 8.7 Hz, 1H), 7.60 (d, d, d, J=2.1, 7.5, 9.6 Hz, 1H), 7.23 (d, J=8.1 Hz, 1H), 7.12 (d, d, d, J=1.5, 4.8, 6.3 Hz, 1H), 6.44-6.41 (m, 2H), 3.83 (s, 3H), 3.45 (t, J=7.5 Hz, 3=2H), 3.22 (t, J=7.8 Hz, 2H).

EXAMPLE 5

1-(2-hydroxyphenyl)-3-(5-methylpyridin-2-yl)propan-1-one

The title compound was synthesized using the same procedure as described in example 1.

$^1$H NMR (300 MHz, CDCl$_3$): δ 12.25 (s, 1H), 8.36 (d, J=3.0 Hz, 1H), 7.85 (d, d, J=1.8, 8.4 Hz, 1H), 7.49-7.43 (m, 2H), 7.20 (d, J=9.0 Hz, 1H), 6.97 (d, d, J=2.1, 8.1 Hz, 1H), 6.89 (d, d, J=7.5, 8.1 Hz, 1H), 3.57 (t, J=6.9 Hz, 2H), 3.23 (t, J=6.9 Hz, 2H), 2.32 (s, 3H).

EXAMPLE 6

1-(4-ethoxy-2-hydroxyphenyl)-3-(pyridine-2-yl)propan-1-one

The title compound was synthesized using the same procedure as described in example 1.

$^1$H NMR (300 MHz, CDCl$_3$): δ 12.71 (s, 1H), 8.53 (d, J=5.4 Hz, 1H), 7.73 (d, J=8.7 Hz, 1H), 7.63 (d, d, d, J=1.8, 7.5, 9.6 Hz, 1H), 7.28 (d, J=8.1 Hz, 1H), 7.15 (d, d, J=4.8, 6.3 Hz, 1H), 6.44-6.40 (m, 2H), 4.06 (q, J=7.5 Hz, 2H), 3.48 (t, J=7.8 Hz, 2H), 3.24 (t, J=7.8 Hz, 2H), 1.42 (t, J=7.5 Hz, 3H).

EXAMPLE 7

1-(2-hydroxy-3,5-dimethylphenyl)3-(pyridine-2-yl)propan-1-one

The title compound was synthesized using the same procedure as described in example 1.

$^1$H NMR (300 MHz, CDCl$_3$): δ 12.40 (s, 1H), 8.55 (bd, J=5.2 Hz, 1H), 7.64 (d, d, d, J=1.8, 8.1, 10.2 Hz, 1H), 7.49 (s, 1H), 7.29 (d, J=8.1 Hz, 1H), 7.18-7.14 (m, 2H), 3.57 (t, J=7.5 Hz, 2H), 3.26 (t, J=7.8 Hz, 2H), 2.28 (s, 3H), 2.24 (s, 3H).

EXAMPLE 8

1-(2-hydroxy-5-methylphenyl)-3-(pyridine-2-yl)propan-1-one

The title compound was synthesized using the same procedure as described in example 1.

$^1$H NMR (300 MHz, CDCl$_3$): δ 12.09 (s, 1H), 8.52 (d, J=4.8 Hz, 1H), 7.62-7.57 (m, 2H), 7.28-7.23 (m, 2H), 7.12 (d, d, J=4.8, 7.5 Hz, 1H), 6.86 (d, J=8.4 Hz, 1H), 3.54 (t, J=6.9 Hz, 2H), 3.23 (t, J=6.9 Hz, 2H), 2.28 (s, 3H).

EXAMPLE 9

1-(5-ethyl-2-hydroxyphenyl)-3-(pyridine-2-yl)propan-1-one

The title compound was synthesized using the same procedure as described in example 1.

$^1$H NMR (300 MHz, CDCl$_3$): δ 12.11 (s, 1H), 8.54 (d, J=3.3 Hz, 1H), 7.67-7.61 (m, 2H), 7.32 (d,d, J=2.1, 8.1 Hz, 1H), 7.16 (d, d, J=6.3, 8.4 Hz, 1H), 6.92 (d, J=8.7 Hz, 1H), 3.59 (t, J=6.6 Hz, 2H), 3.27 (t, J=6.6 Hz, 2H), 2.61 (q, J=8.7 Hz, 2H), 1.23 (t, J=7.5 Hz, 3H).

EXAMPLE 10

1-(2-hydroxyphenyl)-3-(3-methylpyridin-2-yl)propan-1-one

The title compound was synthesized using the same procedure as described in example 1.

$^1$H NMR (300 MHz, CDCl$_3$): δ 12.31 (s, 1H), 8.34 (d, J=6.3 Hz, 1H), 7.91 (d, J=6.3 Hz, 1H), 7.49-7.44 (m, 2H), 7.09-7.04 (m, 1H), 6.98 (d, J=9.0 Hz, 1H), 6.91 (d, d, J=7.5, 7.5 Hz, 1H), 3.61 (t, J=7.5 Hz, 2H), 3.23 (t, J=7.5 Hz, 2H), 2.39 (s, 3H).

EXAMPLE 11

1-(2-hydroxy-3,5-dimethylphenyl)3-(pyridine-2-yl)propan-1-one

The title compound was synthesized using the same procedure as described in example 2.

$^1$H NMR (300 MHz, CDCl$_3$): 12.40 (s, 1H), 8.55 (bd, J=5.2 Hz, 1H), 7.64 (d, d, d, J=1.8, 8.1, 10.2 Hz, 1H), 7.49 (s, 1H), 7.29 (d, J=8.1 Hz, 1H), 7.18-7.14 (m, 2H), 3.57 (t, J=7.5 Hz, 2H), 3.26 (t, J=7.8 Hz, 2H), 2.28 (s, 3H), 2.24 (s, 3H).

EXAMPLE 12

1-(2-hydroxy-4-isobutoxyphenyl)-3-(pyridine-2-yl)propan-1-one

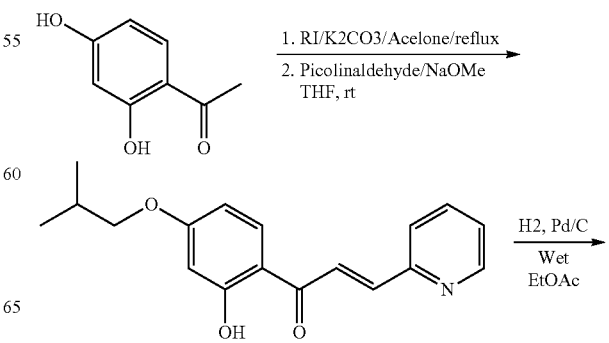

-continued

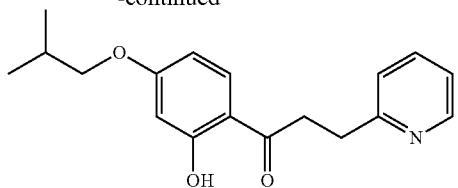

Step 1: To a stirred solution of 1-(2,4-dihydroxyphenyl) ethanone (3.2 g, 21.03 mmol) and K₂CO₃ in 100 mL of acetone at room temperature, the 1-iodo-2-methylpropane (3.6 ml, 21.03 mmol) was added dropwise. The mixture was refluxed for 8 hrs, and then the reaction was kept in 54° C. for overnight. The reaction was cooled down to room temperature and quenched by 1N HCl to pH=7. The aqueous layer was extracted 3× with EtOAc, the organic layers were combined, washed with water, brine and dried (Na₂SO₄). The solvent was removed in vacuo and the residue chromatographed on silica gel 5% EtOAc/Hex to give 1.1 g (25%) of product.

¹H NMR (300 MHz, CDCl₃): δ 12.67 (s, 1H), 7.55 (d, J=8.7 Hz, 1H), 6.36 (d, d, J=2.4, 8.7 Hz, 1H), 6.32 (d, J=2.4 Hz, 1H), 3.68 (d, J=6.6 Hz, 2H), 2.48 (s, 3H), 2.09-21.95 (m, 1H), 0.96 (s, 3H), 0.94 (s, 3H).

Step 2: To a stirred solution of picolinaldehyde (0.6 ml, 5.28 mmol) and NaOMe in Tetrahydrofuran (50 ml) and 1-(2-hydroxy-4-isobutoxyphenyl)ethanone in 5 ml THF was added at room temperature. The mixture was stirred at room temperature for 5 h, 1N HCl was added until pH=7. The aqueous layer was extracted 3× with EtOAc. The organic layers combined, washed with water, brine and dried (Na₂SO₄). The solvent was removed in vacuo and the residue chromatographed on silica gel (25% EtOAc in Hex) to give 0.8 g (51%) of yellow solid.

¹H NMR (300 MHz, CDCl₃): δ 13.37 (s, 1H), 8.72 (d, J=5.1 Hz, 1H), 8.22 (d, J=15.0 Hz, 1H), 7.97 (d, J=9.0 Hz, 1H), 7.84 (d, J=15.0 Hz, 1H), 7.77 (d, d, J=1.8, 7.2 Hz, 1H), 7.50 (d, J=8.1 Hz, 1H), 7.33 (d, d, J=4.8, 7.8 Hz, 1H), 6.51 (d, d, J=2.4, 9.0 Hz, 1H), 6.47 (d, J=2.7 Hz, 1H), 3.80 (d, J=6.6 Hz, 2H), 2.20-2.07 (m, 1H), 1.60 (s, 3H), 1.05 (s, 3H).

Step 3: In a 200 mL round-bottomed flask, (E)-1-(2-hydroxy-4-isobutoxyphenyl)-3-(pyridin-2-yl)prop-2-en-1-one (1.08 g, 3.63 mmol) and 80 mg of 10% Pd/C was mixed together in wet EtOAc (50 ml). Hydrogenation was conducted at atmospheric pressure room temperature until the starting material was gone. The catalyst was filtered and the crude was purified by chromatography on silica gel (25% EtOAc/hexane) to provide 0.92 g of final compound (82%) as off white solid.

¹H NMR (300 MHz, CDCl₃): δ 12.73 (s, 1H), 8.52 (d, J=4.8 Hz, 1H), 7.72 (d, J=9.0 Hz, 1H), 7.61 (d, d, d, J=2.4, 7.8, 9.6 Hz, 1H), 7.25 (d, J=7.8 Hz, 1H), 7.13 (d, d, d, J=1.5, 4.8, 6.0 Hz, 1H), 6.43 (d, d, J=2.1, 8.4 Hz, 1H), 6.39 (d, J=2.7 Hz, 1H), 3.75 (d, J=7.2 Hz, 2H), 3.46 (t, J=7.2 Hz, 2H), 3.23 (t, J=6.9 Hz, 2H), 2.16-2.02 (m, 1H), 1.02 (d, J=7.2 Hz, 6H).

EXAMPLE 13

1-(4-cyclopropylmethoxy)-2-hydroxyphenyl)-3-(pyridine-2-yl)propan-1-one

The title compound was synthesized using the same procedure as described in example 11.

¹H NMR (300 MHz, CDCl₃): δ 12.61 (s, 1H), 8.42 (d, J=5.7 Hz, 1H), 7.52 (d, d, d, J=1.8, 7.8, 9.6 Hz, 1H), 7.16 (d, J=7.5 Hz, 1H), 7.04 (d, d, J=4.8, 7.2 Hz, 1H), 6.34 (d, d, J=2.7, 9.0 Hz, 1H), 6.28 (d, J=2.4 Hz, 1H), 3.73 (d, J=6.9 Hz, 2H), 3.37 (t, J=7.2 Hz, 2H), 3.13 (t, J=7.5 Hz, 2H), 1.24-1.11 (m, 1H), 0.59-0.53 (m, 2H), 0.29-0.23 (m, 2H).

EXAMPLE 14

1-(4-(cyclopentyloxy)-2-hydroxyphenyl)-3-(pyridine-2-yl)propan-1-one

The title compound was synthesized using the same procedure as described in example 11.

¹H NMR (300 MHz, CDCl₃): δ 12.74 (s, 1H), 8.53 (d, J=4.8 Hz, 1H), 7.74-7.70 (m, 1H), 7.62 (d, d, d, J=2.1, 8.1, 9.9 Hz, 1H), 7.26 (d, J=7.8 Hz, 1H), 7.14 (d, d, d, J=1.2, 4.8, 7.5 Hz, 1H), 6.41-6.37 (m, 2H), 4.80-4.76 (m, 1H), 3.47 (t, J=7.5 Hz, 2H), 3.23 (t, J=7.5 Hz, 2H), 2.01-1.78 (m, 8H).

EXAMPLE 15

1-(4-hydroxybenzo[d][1,3]dioxol-5-yl)-3-(pyridin-2-yl)propan-1-one

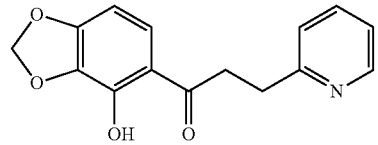 [SMILES: O=C(CCc1ccccn1)c1ccc2c(c1O)OCO2]

Step 1

1-(4-hydroxybenzo[d][1,3]dioxol-5-yl)ethanone (1.8 g, 9.99 mmol) was dissolved in THF (40 ml) to give a colorless solution. Sodium methanolate 30% (5 g, 27.8 mmol) was added. Reaction mixture became dark green colored. After 15 min. stirring at room temperature 1.1 g (10 mmol) of picolinaldehyde dissolved in 10 ml THF was added dropwise during 10 min. The addition was started at 22° C. and was slightly exothermic. Stirring at room temperature was continued for another 3 hrs. Mixture was diluted with diethyl ether and the pH was adjusted to pH 6 with a concentrated hydrochloric acid solution while vigorously stirring. The color changes from dark green to orange/red. After 5 minutes the formed solids were filtered. Solids were stirred with 100 mL of methanol and the remaining solids (mainly NaCl) were filtered again. The filtrate was evaporated and the residue was taken up in a mixture of diethylether and methanol. Solids were filtered and dried to yield 1.7 g of an orange powder. To remove the small amounts of impurities the orange product was stirred with chloroform for 10 minutes, filtered and dried to yield 1.5 g (47%) of the (E)-1-(4-hydroxybenzo[d][1,3] dioxol-5-yl)-3-(pyridin-2-yl)prop-2-en-1-one.

¹H-NMR in DMSO-d6: 6.17 (2H, O—CH2-O, s), 6.72 (1H, CO—CH=, d), 7.60 (1H, aromatic, m), 7.83 (1H, aromatic, d), 7.94 (1H, CO—CH═CH—, d), 8.09-8.13 (2H, aromatic, m), 8.35 (1H, aromatic, d), 8.75 (1H, aromatic N—CH, d), 9.83 (1H, OH, s)

The 1-(4-hydroxybenzo[d][1,3]dioxol-5-yl)ethanone was prepared by the reaction of trihydroxy acetophenone with diiodomethane.

Step 2

(E)-1-(4-hydroxybenzo[d][1,3]dioxol-5-yl)-3-(pyridin-2-yl)prop-2-en-1-one (0.5 g, 1.857 mmol) was added to methanol (50 ml) to give a yellow solution. Palladium on carbon (0.05 g) was added. Product was hydrogenated while stirring till conversion was completed (checked by TLC). The reaction mixture was filtered, evaporated and the solid residue was washed with diethylether, and dried to yield 0.3 g (57%) of the title compound.

1H-NMR in DMSO-d6: 3.11 (2H, CH2-C═N, t), 3.49 (2H, CO—CH2-, t), 6.13 (2H, O—CH2-O, s), 6.64 (1H, aromatic, d), 7.19 (1H, aromatic, m), 7.33 (1H, aromatic, d), 7.67-7.70 (2H, aromatic, m), 8.44 (1H, aromatic N—CH, d), 9.83 (1H, OH, s)

EXAMPLE 16

1-(2-methoxyphenyl)-3-(pyridin-2-yl)propan-1-one

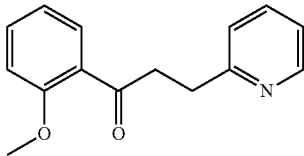 [SMILES: COc1ccccc1C(=O)CCc1ccccn1]

1-(2-methoxyphenyl)ethanone (3 g, 19.98 mmol), pyridin-2-ylmethanol (2.180 g, 19.98 mmol), and potassium hydroxide (1.121 g, 19.98 mmol) were added to dioxane (50 ml) to give a yellow suspension. RuCl2 (Me2SO)4 (0.2 g) was added. Reaction mixture was heated at 80° C. for 1 hour.

Reaction mixture was filtered through Silicagel to remove catalyst and KOH. The filtrate was evaporated and the residue was purified by column chromatography.

Eluent:ethylacetate:heptane=3:1. 0.2 g (4%) of the title compound was obtained.

1H-NMR in chloroform,d: 3.20 (2H, CO—CH2-, t), 3.47 (2H, —CH2-Ar, t), 3.87 (3H, —OCH3, s), 6.95 (2H, aromatic, m), 7.1 (1H, aromatic, m), 7.23 (1H, aromatic, d), 7.45 (1H, aromatic, m)

7.58 (1H, aromatic, m), 7.70 (1H, aromatic, d), 8.50 (1H, aromatic N—CH═, d)

EXAMPLE 17

Testing of Compounds

Various compounds prepared in the previous examples were tested.

Two solutions were prepared:

A: a solution of 0.3% NaCl,

B: a solution of 0.3% NaCl and 2 ppm compound as per Table 1.

The samples were tasted by a trained sensory panel composed of 20 women aged between 30 and 60.

TABLE 1

| Compound | Taste description |
| --- | --- |
| 1-(2-hydroxy-4-methylphenyl)-3-(pyridin-2-yl)propan-1-one | Umami, sweet, licorice, savoury |
| 1-(2-hydroxy-4-methoxyphenyl)-3-(pyridin-2-yl)propan-1-one | umami, sweet, salty, longlasting savouryness |
| 1-(2-hydroxyphenyl)-3-(5-methylpyridin-2-yl)propan-1-one | Slightly umami, some green aftertaste, floral |
| 1-(4-ethoxy-2-hydroxyphenyl)-3-(pyridine-2-yl)propan-1-one | Umami, floral |
| 1-(4-cyclopropylmethoxy)-2-hydroxyphenyl)-3-(pyridine-2-yl)propan-1-one | Umami |
| 1-(2-hydroxy-4-isobutoxyphenyl)-3-(pyridine-2-yl)propan-1-one | Umami, sweet, salty, bouillon, lingering, intense |
| 1-(2-hydroxy-4,5-dimethylphenyl)-3-(pyridine-2-yl)propan-1-one | Umami, sweet, savoury, salty |
| 1-(2-methoxyphenyl)-3-(pyridin-2-yl)propan-1-one | Umami, slightly bitter |
| 1-(2-hydroxyphenyl)-3-(3-methylpyridin-2-yl)propan-1-one | Slightly umami, savoury, meaty |
| 1-(4-hydroxybenzo[d][1,3]dioxol-5-yl)-3-(pyridin-2-yl)propan-1-one | Clearly umami, slightly yeasty, bouillon |
| 1-(2-hydroxy-3,5-dimethylphenyl)-3-(pyridine-2-yl)propan-1-one | Umami |
| 1-(4-(cyclopentoxy)-2-hydroxyphenyl)-3-(pyridine-2-yl)propan-1-one | Umami |
| 1-(2-hydroxy-5-methylphenyl)-3-(pyridine-2-yl)propan-1-one | Umami |
| 1-(2-methoxyphenyl)-3-(pyridine-2-yl)propan-1-one | Umami, slightly bitter |
| 1-(5-ethyl-2-hydroxyphenyl)-3-(pyridine-2-yl)propan-1-one | Umami, slightly bitter |
| 1-(2-hydroxy-3,5-dimethylphenyl)3-(pyridine-2-yl)propan-1-one. | Umami |

EXAMPLE 18

Comparative Test with MSG

Two solutions were prepared:
A: a solution of 0.3% NaCl and 0.03% MSG,
B: a solution of 0.3% NaCl, 0.03% MSG and 5 ppm of 1-(4-hydroxybenzo[d][1,3]dioxol-5-yl)-3-(pyridin-2-yl)propan-1-one.
The samples were tasted by a trained sensory panel composed of 20 women aged between 30 and 60.
Solution A: salty, umami.
Solution B: salty, umami, more bouillon-like, more complex, less sweet.

EXAMPLE 19

Tomato Soup Formulation

A tomato soup mix was prepared from 9.4 g sodium chloride, 1 g MSG, 0.08 g ribonucleotides (ex yeast), 32 g tomato powder (ex Spreda), 25.1 g glucose, 21 g starch (Ultrasperse™ 5 ex National Starch), 5 g palm fat powder, 3 g yeast powder, 1 g onion powder, 0.15 g carrot powder, 0.05 g ground white pepper, 0.3 g celery extract powder, 0.05 g ground laurel leaf powder, and 1.85 g sucrose. 25 g of the well-mixed ingredients was added to 250 g of boiling water and stirred until completely dissolved, to give a reference soup.

The reference soup was compared with a batch of the same soup containing 1.5 ppm of 1-(2-hydroxy-4-isobutoxyphenyl)-3-(pyridine-2-yl)propan-1-one. A small group of flavourists (2 male, 2 female) tasted the soups and agreed that the test soup was more umami, had a clear lingering effect, was more salty and was more complex than the reference soup.

EXAMPLE 20

Potato Chips

Plain potato chips were prepared.
One part was flavoured with 1.2% sodium chloride (sample A),
One part was flavoured with 1.2% sodium chloride and 0.3% MSG (sample B),
One part was flavoured with 1.2% sodium chloride and 2 ppm of 1-(2-hydroxy-4-methylphenyl)-3-(pyridin-2-yl)propan-1-one (sample C).
The samples were tasted by a trained sensory panel composed of 20 women aged between 30 and 60.
The panel preferred sample C over the other two samples.
Sample A was described as salty, sample B as salty and umami and sample C as salty, strong umami, long lasting, savoury, bouillon.

EXAMPLE 21

Tomato Ketchup

A tomato ketchup was prepared from 19% tomato paste (28-30% dry weight), 8% vinegar (15%), 3% sodium chloride, 20% sugar and 50% water.
To one-half of the batch was added 2 ppm of 1-(2-hydroxy-4-methoxyphenyl)-3-(pyridin-2-yl)propan-1-one.

A small group of flavourists (2 male, 2 female) tasted the ketchups and agreed that the test ketchup tasted clearly more umami, more salty and had a pleasant savoury note compared with that of the ketchup without the compound.

EXAMPLE 22-24

The following compositions are made and tested. Using a bench-top tasting panel (consisting of 10 panelists—flavorists, application experts), panelists were asked to record the sensory attribute differences (umami) between the samples. All samples were tasted blind and ranked on umami.

EXAMPLE 22

Commercial Organic Chicken Broth (Swanson's Certified Organic Chicken Broth—No Added MSG, Contains about 0.4% Sugars)

| Control | |
|---|---|
| Ingredient | % (by weight) |
| Commercial Organic Chicken Broth (550 mg Na/240 mL serving) | 100 |

| Reference | |
|---|---|
| Ingredient | % (by weight) |
| MSG | 0.05 |
| Commercial Organic Chicken Broth (550 mg Na/240 mL serving) | Balance to 100 |

| Ingredient 1-(2-hydroxy-4-methylphenyl)-3-(pyridin-2-yl)propan-1-one | |
|---|---|
| Ingredient | % (by weight) |
| 1-(2-hydroxy-4-methylphenyl)-3-(pyridin-2-yl)propan-1-one; | 0.001 |
| Commercial Organic Chicken Broth (550 mg Na/240 mL serving) | Balance to 100 |

Sensory findings: Panelists preferred 0.001% of 1-(2-hydroxy-4-methylphenyl)-3-(pyridin-2-yl)propan-1-one in this base. In a blind ranking of 6 different samples MSG was the highest umami with 1-(2-hydroxy-4-methylphenyl)-3-(pyridin-2-yl)propan-1-one finishing $2^{nd}$ and Control finishing $5^{th}$.

| Ingredient 1-(2-hydroxy-4-isobutoxyphenyl)-3-(pyridine-2-yl)propan-1-one | |
|---|---|
| Ingredient | % (by weight) |
| 1-(2-hydroxy-4-isobutoxyphenyl)-3-(pyridine-2-yl)propan-1-one | 0.002 |
| Commercial Organic Chicken Broth (550 mg Na/240 mL serving) | Balance to 100 |

Sensory findings: Panelists preferred 0.002% of 1-(2-hydroxy-4-isobutoxyphenyl)-3-(pyridine-2-yl)propan-1-one in this base. In a blind ranking of 6 different samples MSG was the highest umami with 1-(2-hydroxy-4-isobutoxyphenyl)-3-(pyridine-2-yl)propan-1-one finishing $3^{rd}$ and Control finishing $5^{th}$.

| Ingredient 1-(2-hydroxy-4-methoxyphenyl)-3-(pyridin-2-yl)propan-1-one | |
| --- | --- |
| Ingredient | % (by weight) |
| 1-(2-hydroxy-4-methoxyphenyl)-3-(pyridin-2-yl)propan-1-one | 0.002 |
| Commercial Organic Chicken Broth (550 mg Na/240 mL serving) | Balance to 100 |

Sensory findings: Panelists preferred 0.002% of 1-(2-hydroxy-4-methoxyphenyl)-3-(pyridin-2-yl)propan-1-one in this base. In a blind ranking of 6 different samples MSG was the highest umami with 1-(2-hydroxy-4-methoxyphenyl)-3-(pyridin-2-yl)propan-1-one finishing $4^{th}$ and Control finishing $5^{th}$.

EXAMPLE 23

Model Chicken Broth—No MSG Added, No Sugar Added

The model chicken broth powder was prepared from 11.9 g chicken fat, 23.81 g salt, 14.29 g sugar, 0.95 g onion powder, 49.01 g chicken powder, 0.04 g turmeric powder. To prepare the model chicken broth 2.0 g of powder was mixed 98.0 g hot water.

| Control | |
| --- | --- |
| Ingredient | % (by weight) |
| Model Chicken Broth (653 mg Na/240 mL serving) | 100 |

| Reference | |
| --- | --- |
| Ingredient | % (by weight) |
| MSG | 0.05 |
| Model Chicken Broth (653 mg Na/240 mL serving) | Balance to 100 |

| Ingredient 1-(2-hydroxy-4-methylphenyl)-3-(pyridin-2-yl)propan-1-one | |
| --- | --- |
| Ingredient | % (by weight) |
| 1-(2-hydroxy-4-methylphenyl)-3-(pyridin-2-yl)propan-1-one | 0.0005 |
| Model Chicken Broth (653 mg Na/240 mL serving) | Balance to 100 |

Sensory findings: Panelists preferred 0.0005% of 1-(2-hydroxy-4-methylphenyl)-3-(pyridin-2-yl)propan-1-one in this base. In a blind ranking of 6 different samples MSG was the highest umami with 1-(2-hydroxy-4-methylphenyl)-3-(pyridin-2-yl)propan-1-one finishing $3^{rd}$ and Control finishing $5^{th}$.

| Ingredient 1-(2-hydroxy-4-isobutoxyphenyl)-3-(pyridine-2-yl)propan-1-one | |
| --- | --- |
| Ingredient | % (by weight) |
| -(2-hydroxy-4-isobutoxyphenyl)-3-(pyridine-2-yl)propan-1-one | 0.001 |
| Model Chicken Broth (653 mg Na/240 mL serving) | Balance to 100 |

Sensory findings: Panelists preferred 0.001% of -(2-hydroxy-4-isobutoxyphenyl)-3-(pyridine-2-yl)propan-1-one in this base. In a blind ranking of 6 different samples MSG was the highest umami with -(2-hydroxy-4-isobutoxyphenyl)-3-(pyridin-2-yl)propan-1-one finishing $4^{th}$ and Control finishing $5^{th}$.

| Ingredient 1-(2-hydroxy-4-methoxyphenyl)-3-(pyridin-2-yl)propan-1-one | |
| --- | --- |
| Ingredient | % (by weight) |
| 1-(2-hydroxy-4-methoxyphenyl)-3-(pyridin-2-yl)propan-1-one | 0.001 |
| Model Chicken Broth (653 mg Na/240 mL serving) | Balance to 100 |

Sensory findings: Panelists preferred 0.001% of 1-(2-hydroxy-4-methoxyphenyl)-3-(pyridin-2-yl)propan-1-one in this base. In a blind ranking of 6 different samples MSG was the highest umami with 1-(2-hydroxy-4-methoxyphenyl)-3-(pyridin-2-yl)propan-1-one finishing $2^{nd}$ and Control finishing $5^{th}$.

EXAMPLE 24

Model Chicken Broth—No MSG Added, 0.3% Sugar Added

The model chicken broth powder was prepared from 11.9 g chicken fat, 23.81 g salt, 14.29 g sugar, 0.95 g onion powder, 49.01 g chicken powder, 0.04 g turmeric powder. To prepare the model chicken broth 2.0 g of powder was mixed 98.0 g hot water.

| Control | |
| --- | --- |
| Ingredient | % (by weight) |
| Model Chicken Broth - sugar added (653 mg Na/240 mL serving) | 100 |

| Reference | |
| --- | --- |
| Ingredient | % (by weight) |
| MSG | 0.05 |
| Model Chicken Broth - sugar added (653 mg Na/240 mL serving) | Balance to 100 |

| Ingredient 1-(2-hydroxy-4-methylphenyl)-3-(pyridin-2-yl)propan-1-one | |
| --- | --- |
| Ingredient | % (by weight) |
| 1-(2-hydroxy-4-methylphenyl)-3-(pyridin-2-yl)propan-1-one | 0.0010 |
| Model Chicken Broth - sugar added (653 mg Na/240 mL serving) | Balance to 100 |

Sensory findings: Panelists preferred 0.001% of 1-(2-hydroxy-4-methylphenyl)-3-(pyridin-2-yl)propan-1-one in this base. In a blind ranking of 6 different samples MSG was the highest umami with 1-(2-hydroxy-4-methylphenyl)-3-(pyridin-2-yl)propan-1-one finishing $5^{th}$ and Control finishing $6^{th}$.

| Ingredient: 1-(2-hydroxy-4-isobutoxyphenyl)-3-(pyridine-2-yl)propan-1-one | |
| --- | --- |
| Ingredient | % (by weight) |
| 1-(2-hydroxy-4-isobutoxyphenyl)-3-(pyridine-2-yl)propan-1-one | 0.002 |
| Model Chicken Broth - sugar added (653 mg Na/240 mL serving) | Balance to 100 |

Sensory findings: Panelists preferred 0.002% of compound 1-(2-hydroxy-4-isobutoxyphenyl)-3-(pyridine-2-yl)propan-1-one in this base. In a blind ranking of 6 different samples MSG was the highest umami with 1-(2-hydroxy-4-isobutoxyphenyl)-3-(pyridine-2-yl)propan-1-one finishing $4^{th}$ and Control finishing $6^{th}$.

| Ingredient 1-(2-hydroxy-4-methoxyphenyl)-3-(pyridin-2-yl)propan-1-one | |
|---|---|
| Ingredient | % (by weight) |
| 1-(2-hydroxy-4-methoxyphenyl)-3-(pyridin-2-yl)propan-1-one | 0.002 |
| Model Chicken Broth - sugar added (653 mg Na/240 mL serving) | Balance to 100 |

Sensory findings: Panelists preferred 0.002% of 1-(2-hydroxy-4-methoxyphenyl)-3-(pyridin-2-yl)propan-1-one in this base. In a blind ranking of 6 different samples MSG was the highest umami with 1-(2-hydroxy-4-methoxyphenyl)-3-(pyridin-2-yl)propan-1-one finishing 3$^{rd}$ and Control finishing 6$^{th}$.

| Ingredient 1-(2-hydroxy-4,5-dimethylphenyl)-3-(pyridine-2-yl)propan-1-one | |
|---|---|
| Ingredient | % (by weight) |
| 1-(2-hydroxy-4,5-dimethylphenyl)-3-(pyridine-2-yl)propan-1-one | 0.002 |
| Model Chicken Broth - sugar added (653 mg Na/240 mL serving) | Balance to 100 |

Sensory findings: Panelists preferred 0.002% of 1-(2-hydroxy-4,5-dimethylphenyl)-3-(pyridine-2-yl)propan-1-one in this base. In a blind ranking of 6 different samples MSG was the highest umami with 1-(2-hydroxy-4,5-dimethylphenyl)-3-(pyridine-2-yl)propan-1-one finishing 2$^{nd}$ and Control finishing 6$^{th}$. - in this base at this level. 1-(2-hydroxy-4,5-dimethylphenyl)-3-(pyridine-2-yl)propan-1-one performed well when evaluating for umami.

In certain embodiments there is provided a compound (including salts thereof) according to Formula I

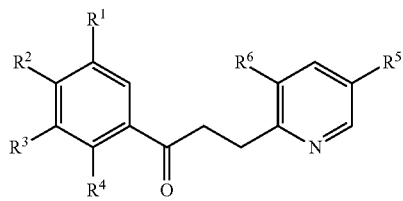

in which $R^1$ comprises H, methyl or ethyl;

$R^2$ comprises H, OH, fluorine, $C_1$-$C_4$ linear or branched alkyl, $C_1$-$C_6$ alkoxy wherein the alkyl group is linear or branched, or a $C_3$-$C_5$ cycloalkyl moiety;

$R^3$ comprises H, methoxy, methyl or ethyl;

or $R^2$ and $R^3$ together form a bridging moiety —O—CH$_2$—O— between the phenyl carbon atoms to which they are connected;

$R^4$ comprises OH or methoxy; and $R^5$ and $R^6$ independently comprise H or methyl;

$R^1$, $R^2$, $R^3$, $R^4$, $R^5$ and $R^6$ are such that, (i) when $R^2$ and $R^3$ together form a bridging moiety —O—CH$_2$—O— between the phenyl carbon atoms to which they are connected, $R^1$, $R^5$, $R^6$ are H, and $R^4$ is OH; and (ii) when $R^4$ is OH and $R^1$-$R^3$ are H, at least one of $R^5$ or $R^6$ is methyl.

In a particular embodiment, $R^3$ is selected from H and methoxy.

In a particular embodiment, $R^2$ comprises H, OH, fluorine, methyl, $C_1$-$C_6$ alkoxy wherein the alkyl group is linear or branched, or a $C_3$-$C_5$ cycloalkyl moiety.

In other particular embodiments, $R^2$ consists of a $C_3$-$C_5$ cycloalkyl moiety.

In other particular embodiments, $R^1$ comprises H or methyl, $R^2$ comprises methyl, methoxy or isobutyloxy, $R^3$ is H, $R^4$ is OH, and $R^5$ and $R^6$ are H.

These compounds confer desirable umami taste sensations on compositions intended to be taken orally, as disclosed above.

Although the embodiments have been described in detail through the above description and the preceding examples, these examples are for the purpose of illustration only and it is understood that variations and modifications can be made by one skilled in the art without departing from the scope of the disclosure. It should be understood that the embodiments described above are not only in the alternative, but can be combined.

The invention claimed is:

1. A umami flavouring comprising a compound or salt thereof selected from the group consisting of:

1-(2-hydroxy-4,5-dimethylphenyl)-3-(pyridine-2-yl)propan-1-one;

1-(2-hydroxy-4-methylphenyl)-3-(pyridin-2-yl)propan-1-one;

1-(2-hydroxy-4-methoxyphenyl)-3-(pyridin-2-yl)propan-1-one;

1-(2-hydroxy-4-isobutoxyphenyl)-3-(pyridine-2-yl)propan-1-one;

and mixtures thereof, which compound or salt thereof provides umami flavour.

2. A method of providing umami flavour to a consumable composition, comprising the addition to the composition of at least one compound according to claim 1, which compound provides umami flavour.

3. A consumable composition having an umami flavour, comprising a product base and at least one compound according to claim 1, which compound provides umami flavour.

4. The consumable composition according to claim 3, in which the compound is present at a concentration of from about 0.01 to about 100 ppm.

5. The consumable composition according to claim 3, in which the compound is present at a concentration of from about 0.1 to about 50 ppm.

6. The consumable composition according to claim 3, in which the compound is present at a concentration of from about 0.2 to about 10 ppm.

* * * * *